United States Patent [19]

Barney

[11] 4,312,358
[45] Jan. 26, 1982

[54] INSTRUMENT FOR MEASURING AND COMPUTING HEART BEAT, BODY TEMPERATURE AND OTHER PHYSIOLOGICAL AND EXERCISE-RELATED PARAMETERS

[75] Inventor: George M. Barney, Dallas, Tex.

[73] Assignee: Texas Instruments Incorporated, Dallas, Tex.

[21] Appl. No.: 59,801

[22] Filed: Jul. 23, 1979

[51] Int. Cl.³ .............................................. A61B 5/04
[52] U.S. Cl. .................................... 128/670; 128/706; 128/736; 73/490; 235/91 H; 235/92 MT
[58] Field of Search ........................ 128/670, 687–690, 128/706, 707, 710, 736, 905; 272/DIG. 5, DIG. 6; 235/92 MT, 91 H; 340/323, 573; 73/489, 490, 513

[56] References Cited

U.S. PATENT DOCUMENTS

| | | | |
|---|---|---|---|
| 3,395,698 | 8/1968 | Morehouse | 128/707 |
| 3,797,010 | 3/1974 | Adler et al. | 340/323 |
| 3,846,704 | 11/1974 | Bessette | 128/670 X |
| 4,112,928 | 9/1978 | Putsch | 128/707 |
| 4,159,416 | 6/1979 | Brejnik et al. | 128/690 X |
| 4,202,350 | 5/1980 | Walton | 128/680 |

FOREIGN PATENT DOCUMENTS 2400403 7/1975 Fed. Rep. of Germany ...... 128/707

Primary Examiner—Lee S. Cohen
Attorney, Agent, or Firm—Melvin Sharp; Leo N. Heiting; Mark E. Ogram

[57] ABSTRACT

A body-mounted measuring instrument senses the heart beat and inner body temperature of a user. The instrument includes a computing circuit and a timekeeping circuit for calculating elapsed time, total heart beats, pulse rate, and difference in body temperature from a predetermined normal temperature. A display is included for indicating various physiological parameters measured and an alarm system warns the user if an excessive heart rate and/or body temperature condition occurs. The instrument is well-suited for an athlete engaged in activities such as running, swimming and bicycling, not only as a safety device to warn the user of the occurrence of a dangerous condition, but also as a distance measuring and velocity computing device. The instrument computes distance travelled by the athlete during an exercise period based on the total number of heart beats and the increase in body temperature occurring during the exercise period. In addition to distance travelled, elapsed time, velocity, minutes per mile, aerobics points earned, calories expended and other parameters are computed on a real-time basis and selectively displayed.

23 Claims, 17 Drawing Figures

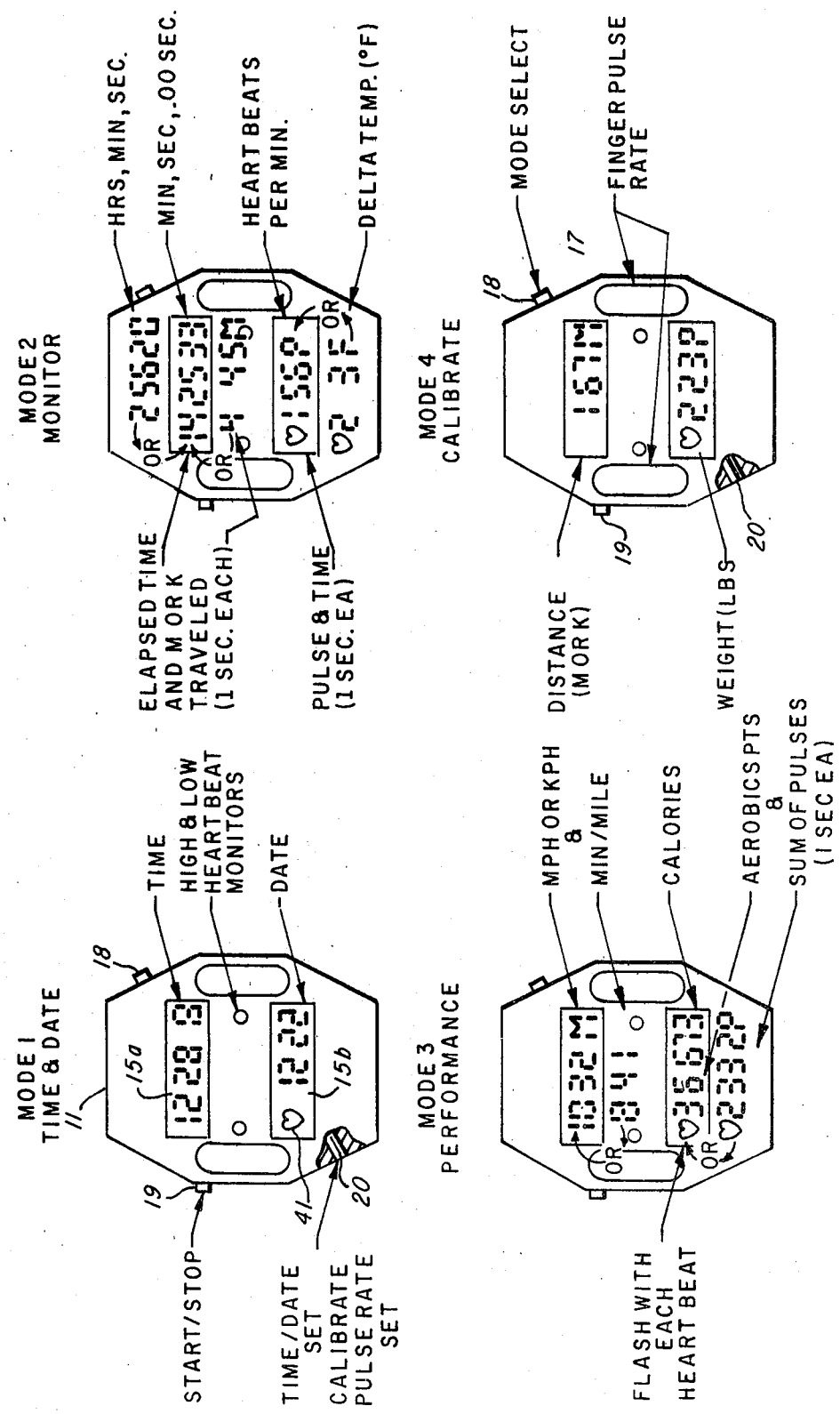

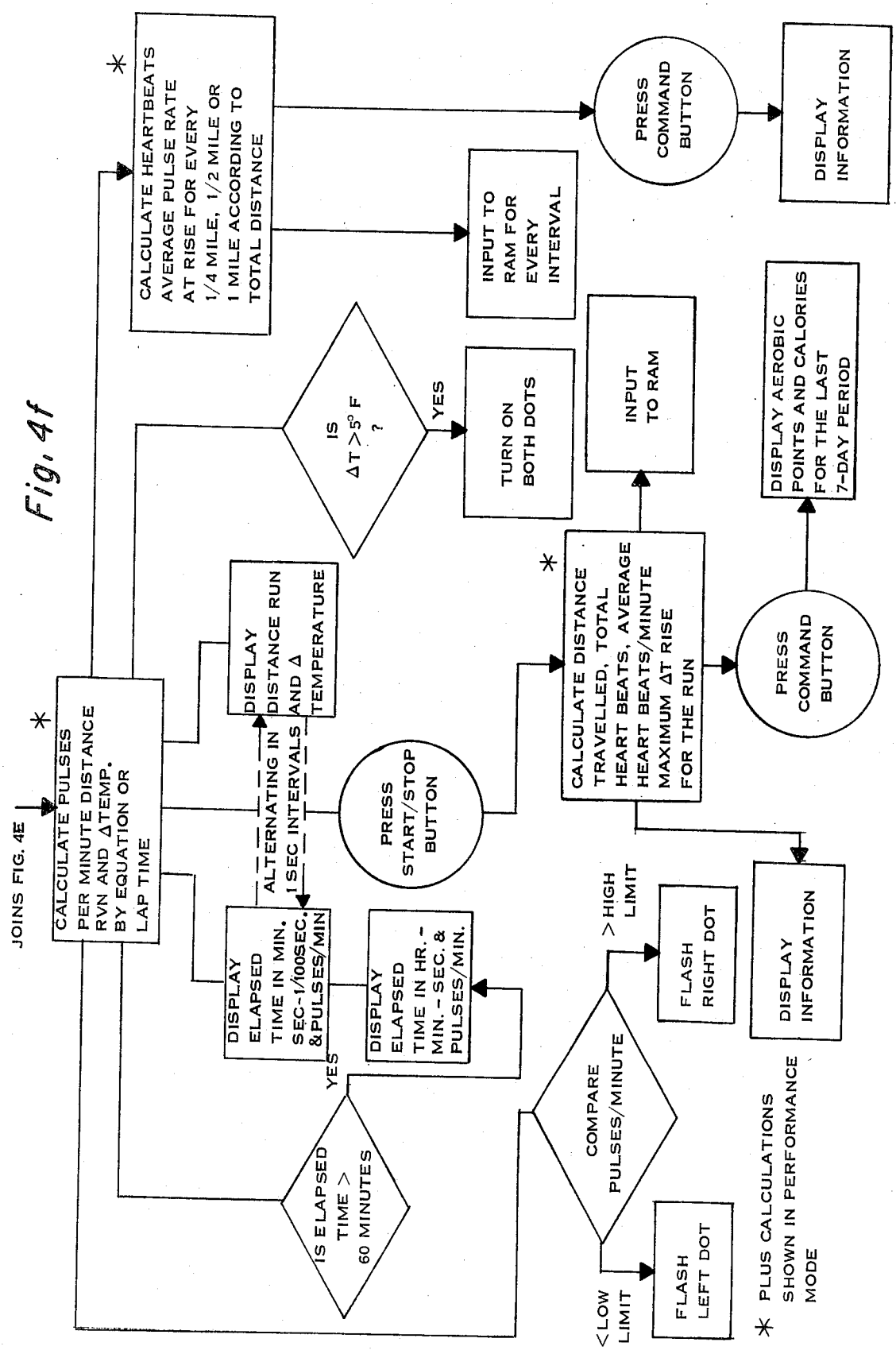

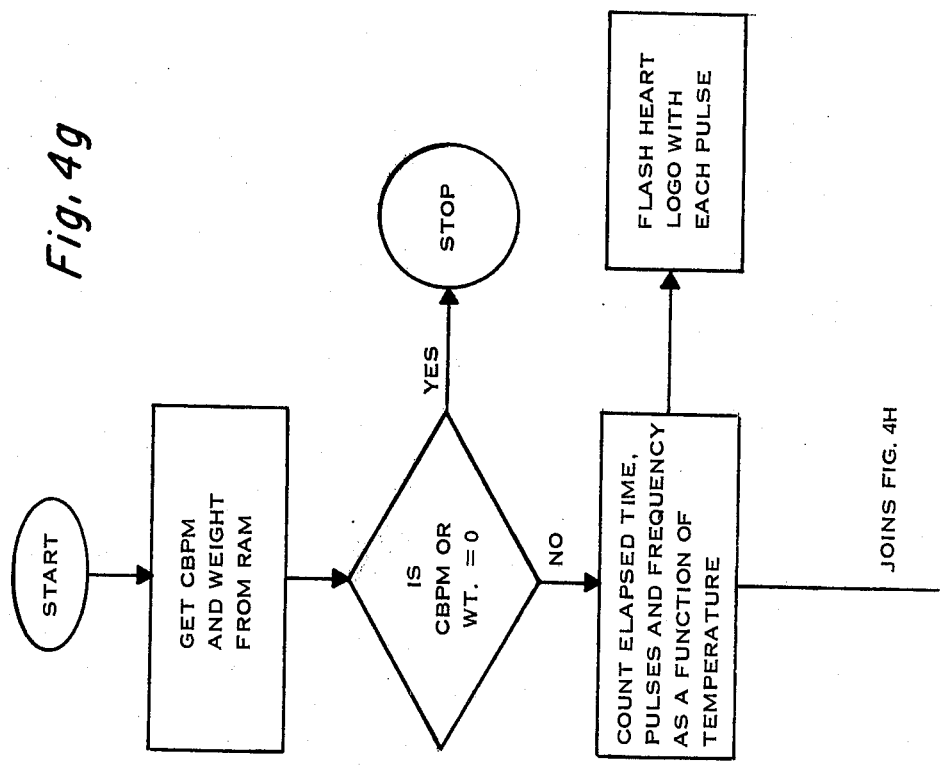

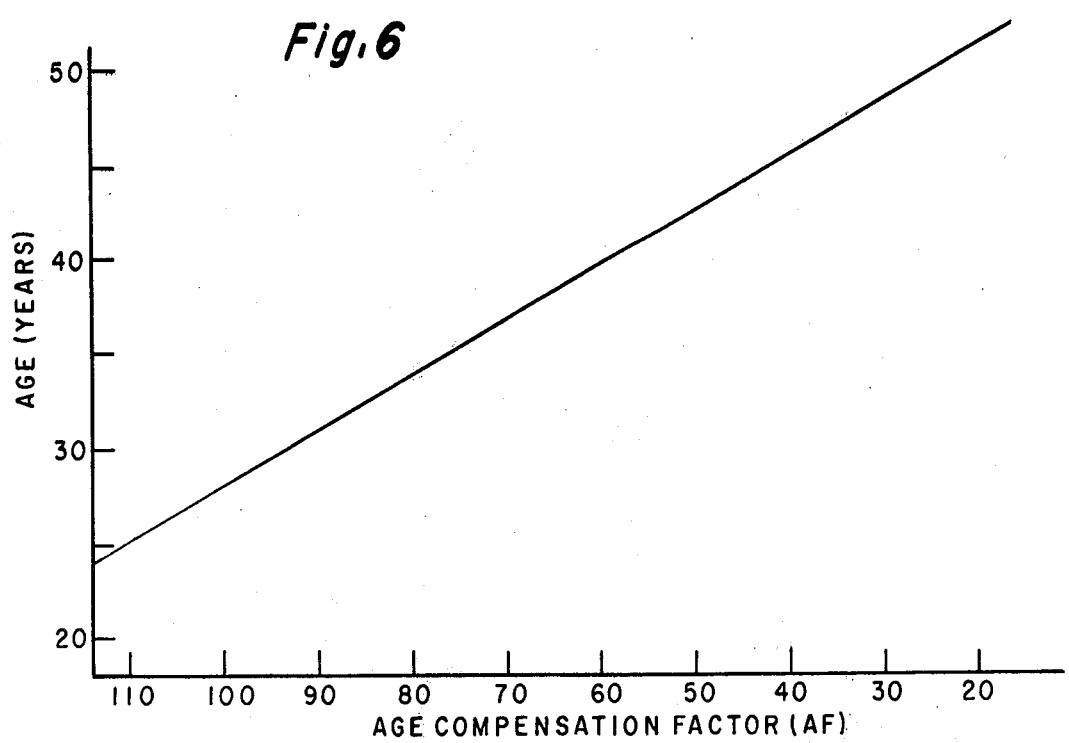

INSTRUMENT FOR MEASURING AND COMPUTING HEART BEAT, BODY TEMPERATURE AND OTHER PHYSIOLOGICAL AND EXERCISE-RELATED PARAMETERS

BACKGROUND OF THE INVENTION

This invention relates to physiological measuring instruments and in particular to an athlete's instrument for measuring body temperature and heart beats and computing pulse rate, distance traveled and velocity as a function thereof.

Instruments for measuring physiological parameters such as heart rate are known in the art. Standard electrocardiogram (EKG) devices are used to sense heart beats and generate an output electrical signal indicative thereof. The outputs generated by EKG's are useful in determining the physiological condition of the subject and particularly in detecting irregularities and/or potential problems in the cardiovascular system.

The number of individuals participating in vigorous athletic activity has been increasing in recent years. During physical exercise, the body requires greater supplies of oxygen and blood flow to meet the increased physical demands. This creates a greater load on the heart and results in increased heart rate, i.e. the number of heart beats in a given time. Overexertion of the heart during exercise can of course lead to adverse physiological effects, but one must reach a certain level of exertion to derive benefit from physical exercise.

Several devices are currently available for monitoring pulse rate activity. One such device is described in U.S. Pat. No. 3,792,700 wherein the pulse rate is measured by placing EKG electrodes under the armpits of the subject. This is well-suited to provide the pulse rate of a sedentary user, but is too cumbersome to be used by one engaged in athletic activity. U.S. Pat. No. 3,902,698 incorporates a pulse rate measuring device with a stationary exercise control system which generates a signal when a particular pulse rate is reached. U.S. Pat. Nos. 3,742,937, 3,807,388 and 3,863,626 describe miniature pulse monitoring devices which can be worn by persons engaged in physical exercise to indicate when a predetermined pulse rate has been exceeded. U.S. Pat. No. 3,978,249 describes a pulse rate indicator which measures both the at rest pulse rate and the pulse rate during physical exercise and generates a comparison signal based on the difference therebetween. When the difference exceeds a predetermined value, an alarm is activated to warn the user that he is overexerting. The device includes a display to indicate changes in the pulse rate activity.

In addition to pulse rate activity, the inner body or "core" temperature of an individual is also a significant factor in assessing the amount of work performed by the body and overall physical stress. Athletes engaged in strenuous exercise, particularly in hot weather, are susceptible to adverse effects such as heat stroke when the core temperature rises to 104° F. As the body performs work, such as during prolonged exercise, the core temperature increases, which in turn causes the heart to beat faster. Thermometers and other temperature measuring devices known in the art must be inserted in a body cavity such as the mouth, armpit or rectal opening to accurately measure core temperature and are not practical for continuous monitoring of the body temperature.

A key parameter for an athlete such as a runner, swimmer, or bicycler, is the distance traveled in a given amount of time. Prior art methods for measuring distance traveled have involved attaching an inertial sensor to the runner to count the number of strides taken and calculate distance based on a predetermined stride length. Inaccuracies often result, however, because the stride length varies depending on a number of physical and psychological factors such as, for example, body weight, body temperature and general physical and mental states. The greater the distance and velocity at which the distance is traversed the greater the work that is performed by the body. Since the total number of heart beats and heart rate achieved are functions of the amount of work and the work rate performed by the body, the distance traveled in a given amount of time and the velocity can also be expressed as functions of the heart rate and the total number of heart beats during exercise.

SUMMARY OF THE INVENTION

It is therefore one object of the invention to provide a heart rate monitoring instrument which is suitable for being worn by one engaged in athletic activity.

It is another object of the invention to provide a body temperature measuring instrument which is suitable for being worn by one engaged in athletic activity.

Yet another object of the invention is to provide an athlete's instrument which computes distance traveled, velocity and other parameters of interest to the athlete as a function of heart beat and inner body temperature measured during an exercise period.

Still another object of the invention is to provide an athlete's instrument which determines calories expended and/or aerobic points accumulated during an exercise period.

It is a further object of the invention to provide an athlete's instrument which warns the user of the occurrence of a dangerously excessive heart beat and/or body temperature condition.

Still a further object of the invention is to provide a physiological measuring instrument having a display for indicating selected physiological parameters.

Yet a further object of the invention is to provide a physiological measuring instrument having a memory device for accumulating and storing results of various physiological measurements for a predetermined period of time.

Still another object of the invention is to provide a physiological monitoring instrument for continually monitoring heart beat and body temperature and computing pulse rate, change in body temperature and other physiological parameters on a real-time basis.

These and other objects are accomplished in accordance with the present invention wherein a body-mountable instrument for determining distance travelled by a user engaged in physical exercise as a function of the user's heart beat and exercise time is provided. The instrument is comprised of heart beat sensing means for detecting the user's heart beats; processing means responsive to the detected heart beats for counting the total number of detected heart beats and for determining the distance travelled by the user during the exercise period; and output indicator means for indicating the distance travelled by the user.

In one embodiment the instrument further includes temperature sensing means for detecting the user's internal body temperature. The processing means is further responsive to the detected temperatures for determining a difference in internal body temperature from a reference temperature and for determining the distance travelled by the user based on the user's heart beats and difference in body temperature.

In another embodiment the output indicator means is a digital display and the cumulative distance travelled by the user is displayed on a real-time basis during the exercise period as well as at the end of the period. In yet another embodiment the instrument includes timekeeping means for keeping track of elapsed time and the processing means is responsive to the detected heart beats and elapsed time information for determining the user's velocity and in still another embodiment the digital processor determines such exercise-related parameters as the user's exercise pace (preferably in minutes per mile), calories expended by the user and aerobics points earned by him.

In a preferred embodiment the instrument is comprised of a wrist-mountable unit of substantially the same size and shape as an electronic wrist watch. Liquid crystal display means is provided for displaying exercise-related parameters to the user on a real-time basis and at the end of the exercise period for the preceding period. The instrument further includes user controllable switch means for controlling the mode of operation of the instrument and for selecting the particular parameters for display.

In another aspect of the invention the instrument is comprised of memory means having a predetermined increment of distance stored therein; user activatable input means for indicating when the user has traversed the distance increment; timekeeping means for keeping track of elapsed time; processing means for determining the user's velocity for the exercise period based on the time elapsed for the user to traverse the distance increment, and output indicator means for indicating the determined parameters to the user.

In one embodiment the exercise-related parameters determined by the processing means include, in addition to the user's velocity, total distance travelled, exercise pace preferably in minutes per mile), calories expended and aerobic points earned by the user. In another embodiment a plurality of sequential distance increments are stored in the memory means and the input means is activated by the user when he completes a respective distance increment. The instrument determines and displays the exercise-related parameters for each distance increment and for the cumulative total thereof. In a preferred embodiment the distance increments correspond to one-quarter mile increments.

BRIEF DESCRIPTION OF THE DRAWINGS

Still further objects and advantages of the invention will be apparent from the detailed description and claims when read in conjunction with the accompanying drawings wherein:

FIGS. 4*a*–4*i* are diagrams depicting five modes of operation of the instrument of the present invention and the information displayed during each mode;

FIG. 6 is a graph of age compensation factor as a function of the athlete's age.

DETAILED DESCRIPTION OF THE INVENTION

Figure 1:
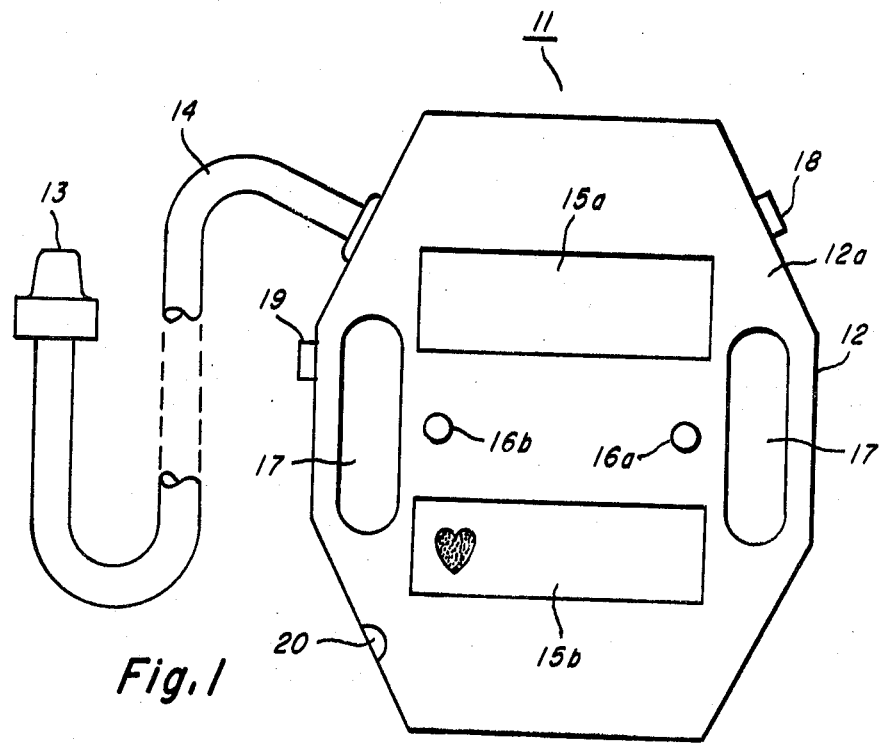
FIG. 1 is a front elevational view of the measuring instrument of the present invention.

Referring to FIG. 1, a physiological measuring instrument 11 which is suitable for being worn by one engaged in athletic activity is shown. Measuring instrument 11 is comprised of a wrist-mounted unit 12 and an ear-mounted sensor 13 which is electrically connected to unit 12 via electrical conductor 14. Ear sensor 13 includes an electrocardiogram (EKG) electrode for detecting heart beats and a thermistor sensor for detecting inner body or "core" temperature. Because several major blood vessels for supplying blood to the brain (such as, for example, the posterior auricular artery; the superficial temporal artery; and the jugular vein) pass by the ear canal and because the temperature of the brain, and not the rest of the body, is the critical factor in determining heat stress, measuring the temperature within the ear canal is superior to measuring temperature at other locations such as the mouth or rectum. A second EKG electrode, which is used in conjunction with the EKG electrode on ear sensor 13 to monitor heart beat is located on the back surface of wrist-mounted unit 12 opposite front surface 12*a*, which is shown in FIG. 1. When unit 12 is properly worn on the wrist, the second EKG electrode is in contact with the dorsal surface of the wrist and front surface 12*a* is visible to the athlete.

Wrist-mounted unit 12 receives heart beat and temperature inputs from ear sensor 13 and computes various parameters of interest to a person engaged in physical exercise such as pulse rate, difference in body temperature, distance traveled, velocity, elapsed time, calories expended and aerobics points accumulated, as will be described in more detail below. Front surface 12*a* has a pair of alphanumeric displays 15*a* and 15*b* which are preferably liquid crystal displays, for simultaneously displaying selected parameters. High and low heart beat monitors 16*a* and 16*b*, respectively, flash on and off periodically when the pulse/heart rate is respectively higher and lower than a predetermined value for which instrument 11 is set. Finger pulse plates 17 are comprised of EKG electrodes which measure the user's pulse rate when he places a finger in contact with each plate 17 and can be used in lieu of ear-mounted sensor 13. Three buttons 18, 19 and 20 extend outwardly from the sides of unit 12 and allow the user to input various parameters into instrument 11 and to select a particular mode of operation of instrument 11 as will be described in more detail below.

Figure 2:
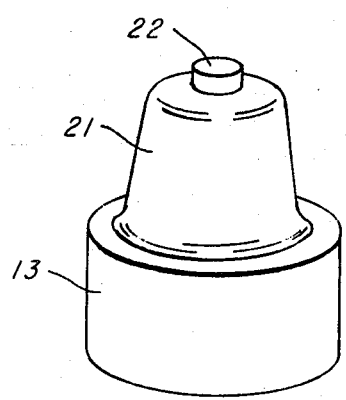
FIG. 2 is a perspective view of the ear-mounted sensor used in the measuring instrument of the present invention.
Figure 3A:
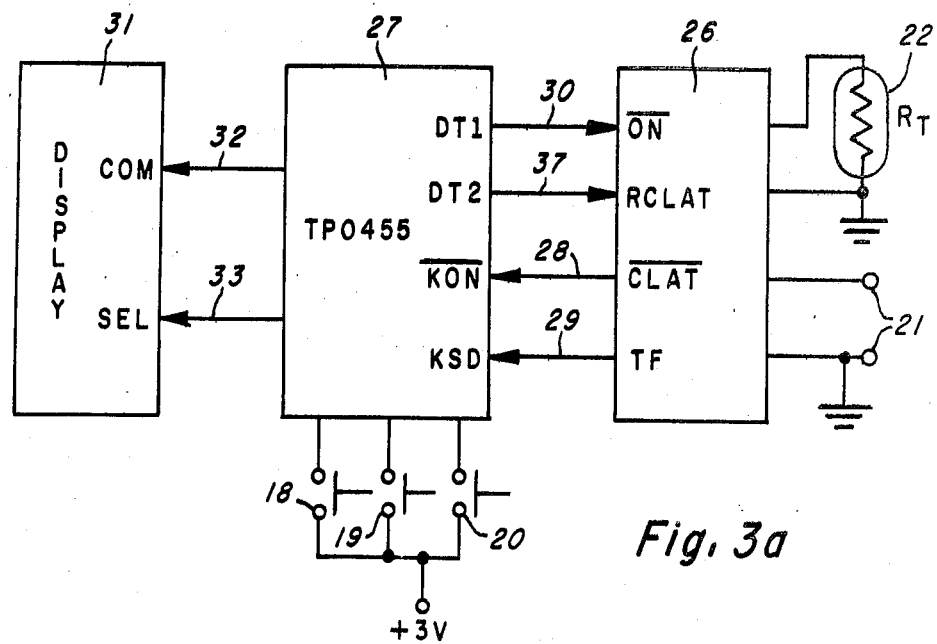
FIG. 3 *a* is a schematic of the electronic circuitry of the present invention in block diagram form.
FIG. 3*b* is a block diagram of the digital processor used in the present invention for storing and processing temperature and heart beat data.
FIG. 3*c* is a block diagram of the sensor chip of the present invention.

As shown in FIG. 2, ear sensor 13 includes EKG electrode 21 for sensing heart beats and thermistor 22 for measuring core temperature when ear sensor 13 is inserted into the user's ear. As previously mentioned, the second EKG sensor is located on wrist-mounted unit 12, in contact with the dorsal surface of the user's wrist. Referring to FIG. 3*a*, sensor chip 26 receives an EKG electrical signal indicative of pulse from EKG electrodes 21 and an indication of temperature from thermistor 22 and transmits pulse and temperature information signals to digital processor 27 via lines 28 and 29, respectively. Digital processor 27 provides electrical power to sensor chip 26 via line 30 and is responsive to the pulse and temperature signals therefrom for computing parameters such as pulse rate, difference in body temperature, distance travelled, velocity and elapsed time. Selected parameters are displayed to the user on display 31, which is comprised of upper display 15a and lower display 15b, as shown in FIG. 1. Display 31 is controlled by digital processor 27, which activates selected alphanumeric characters by means of common line 32 and segment select line 33 to display the results of its computations. Digital processor 27 is further responsive to user inputs via mode select switch 18, start/-stop switch 19 and calibrate/set switch 20 for receiving calibration data and for measuring and displaying selected parameters.

Figure 3C:
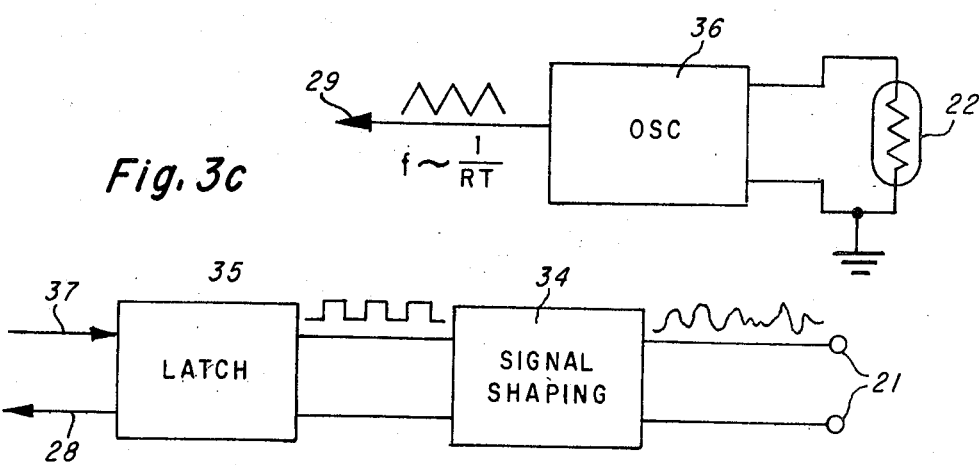
Figure 3B:
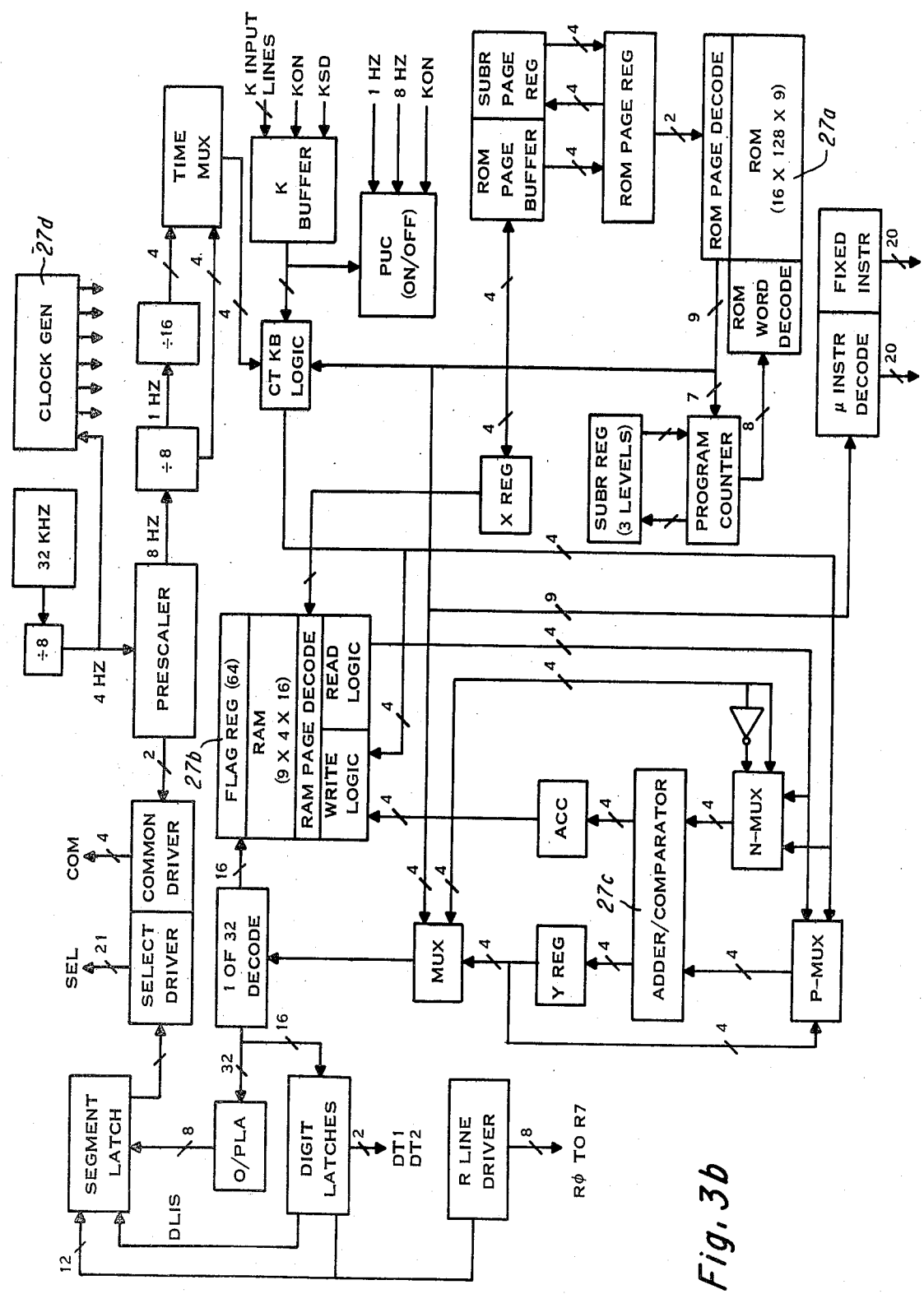

As shown in FIG. 3b, digital processor 27 is preferably a microcomputer having read-only-memory 27a, random-access-memory 27b, adder/comparator 27c, and clocking circuitry 27d on a single CMOS semiconductor chip. It operates at relatively low power, requiring approximately 10 ua of electrical current in the power down mode, when instrument 11 is keeping track of time only and is storing the results of previous computations in memory. It requires approximately 250 ua in the power up mode, when instrument 11 is being used to measure pulse and body temperatures and compute various physiological parameters during an exercise period.

Referring to FIG. 3c, sensor chip 26 includes signal shaping means 34, latch circuit 35 and oscillator 36. The EKG signal from electrodes 21 is shaped to form an essentially square wave pulse signal, each peak of the signal representing one heart beat. The pulse signal sets a cardiac latch in latch circuit 35 each time the user's heart beats. Digital processor 27 resets the cardiac latch via line 37 (see also FIG. 3a) after each heart beat and counts the number of heart beats based on the number of times the cardiac latch is set and reset.

The electrical resistance of thermistor 22 varies inversely proportional to core temperature according to the following expression $$RT = e^{\frac{B}{T}} \quad (1)$$

wherein
RT = electrical resistance
T = temperature (°K.)
B = a material constant (°K.)
e = base of the natural logarithm Oscillator 36 is responsive to the electrical resistance of thermistor 22 for generating an output frequency which is indicative of a change in the electrical resistance of thermistor 22 and hence a difference in core temperature. The output frequency of oscillator 36 is expressed as follows.

$$f = 1/KRT \quad (2)$$

where
f = the output frequency of oscillator 36
K = a constant

The number of oscillations generated during a given time period is detected by digital processor 27 and output frequency f is determined thereby. Digital processor 27 is programmable for calculating the difference in body temperature ($\Delta T$) from the "at rest" temperature $T_1$, which is typically 98.6°±2° F. The actual at rest temperature may be set into digital processor 27 by the user during calibration of instrument 11 or, alternatively, a normalized reference temperature, such as, for example, 98.6° F., may be permanently stored in read-only-memory 27a of digital processor 27.

Temperature $T_1$ corresponds to a particular output frequency $f_1$ of oscillator 36, the relationship being expressed by the following.

$$f_1 = 1/KRT_1 \quad (3)$$

where
$f_1$ = the output frequency at temperature $T_1$
$RT_1$ = the resistance of thermistor 22 at temperature $T_1$ When the body temperature rises, such as during prolonged physical exercise, to a temperature of $T_2$, the output frequency of oscillator 36 increases proportionally to a frequency $f_2$ expressed by the following.

$$f_2 = 1/KRT_2 \quad (4)$$

where
$f_2$ = the output frequency at temperature $T_2$
$RT_2$ = the resistance of thermistor 22 at temperature $T_2$ Combining expressions (3) and (4):

$$\frac{f_2}{f_1} = \frac{RT_1}{RT_2} \quad (5)$$

Referring to expression (1):

$$RT_1 = e^{B/T_1} \text{ and } RT_2 = e^{B/T_2}$$

Therefore:

$$RT_1/RT_2 = e^{B(1/T_1 - 1/T_2)} \quad (6)$$

Combining expressions (5) and (6):

$$\frac{f_2}{f_1} = e^{B(1/T_1 - 1/T_2)}$$

and by rearranging:

$$\ln\left(\frac{f_2}{f_1}\right) = \frac{B \Delta T}{T_1(T_1 + \Delta T)}$$

$$\Delta T = \frac{T_1}{\dfrac{B}{T_1 \ln\left(\dfrac{f_2}{f_1}\right)} - 1} \quad (7)$$

where $\Delta T = T_2 - T_1$ i.e. difference in body temperature ln = natural logarithm.

Using expression (7), digital processor 27 is able to calculate difference in temperature ($\Delta T$) from a normalized at rest temperature ($T_1$) based on the change in the output frequency of oscillator 36 without knowing the actual at rest temperature of the user. In addition to the normalized at rest temperature $T_1$, material constant B, which respresents the relationship of resistance vs. temperature for thermistor 22 is also stored in read-only-memory 27a of digital processor 27.

Assuming Digital Processor 27 is programmed for $T_1 = 98.6°$ F. and B = 3887° K., $\Delta T$ is measureable to an accuracy of $\pm 0.3°$ F. over an extreme body temperature range of 8.4° F. (98.6° F.–107° F.), even when the actual at rest temperature of the user varies $\pm 2°$ F. and thermistor 22 has a loose B tolerance ($\pm 100°$ K. as opposed to $\pm 51°$ K. for most thermometer type thermistors). Thus an inexpensive thermistor 22 with a loose nominal resistance and a relatively loose B tolerance may be used and accurate results still achieved. The use of digital processor 27 to calculate $\Delta T$ makes it unnecessary for thermistor 22 to have a linear temperature vs. resistance profile.

Figure 4B:
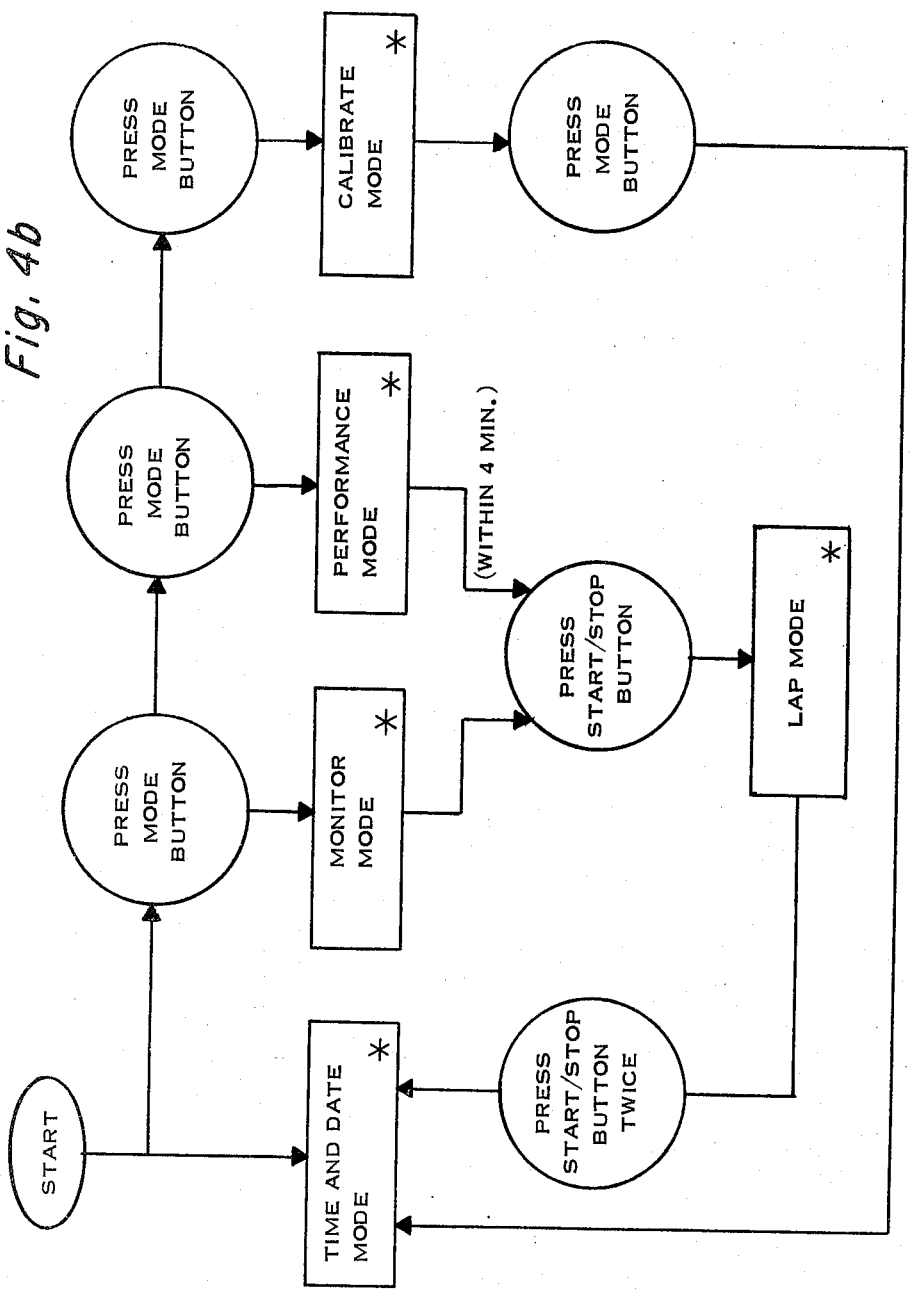
Figure 4C:
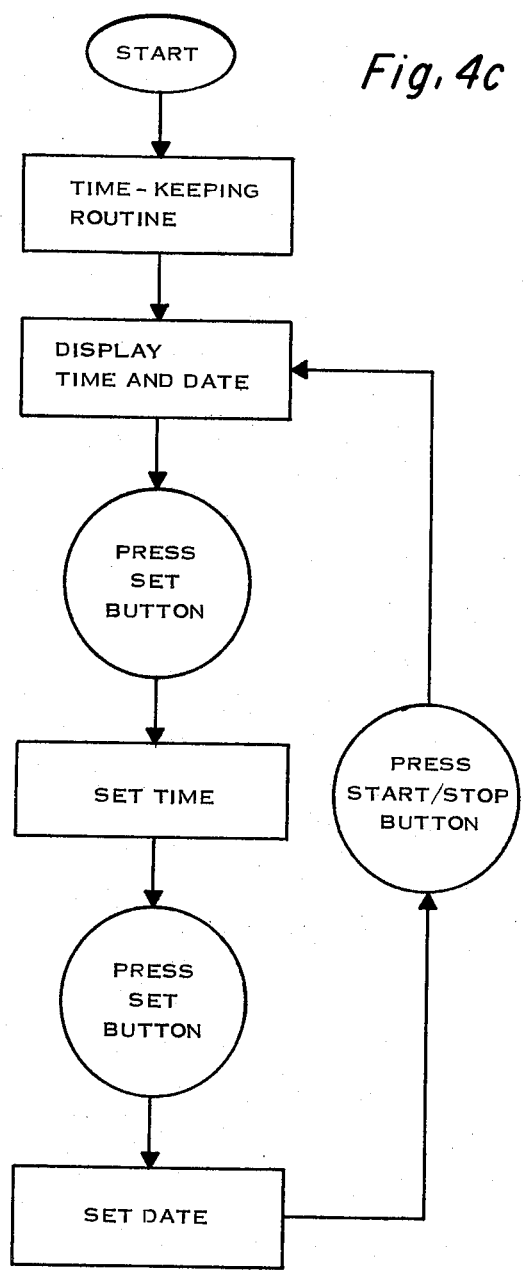

FIGS. 4a and 4b illustrate five modes of operation of instrument 11. Referring to FIG. 4c, when instrument 11 is operated in a Time and Date Mode (Mode 1), calibrate/set switch 20 is pressed and start/stop switch 19 is held down until the correct time of day appears in upper display 15a. Calibrate/set switch 20 is pressed again and start/stop switch 19 is held down until the correct date appears in lower display 15b. Once the correct time and date are set, instrument 11 begins keeping track of time. Time and date information is displayed by pressing start/stop switch 19. The user is able to determine his pulse rate by placing two fingers in contact with respective pulse plates 17 and reading out pulse rate on lower display 15b. Heart logo 41 flashes with each heart beat when the user's fingers are in contact with plates 17.

Figure 4D:
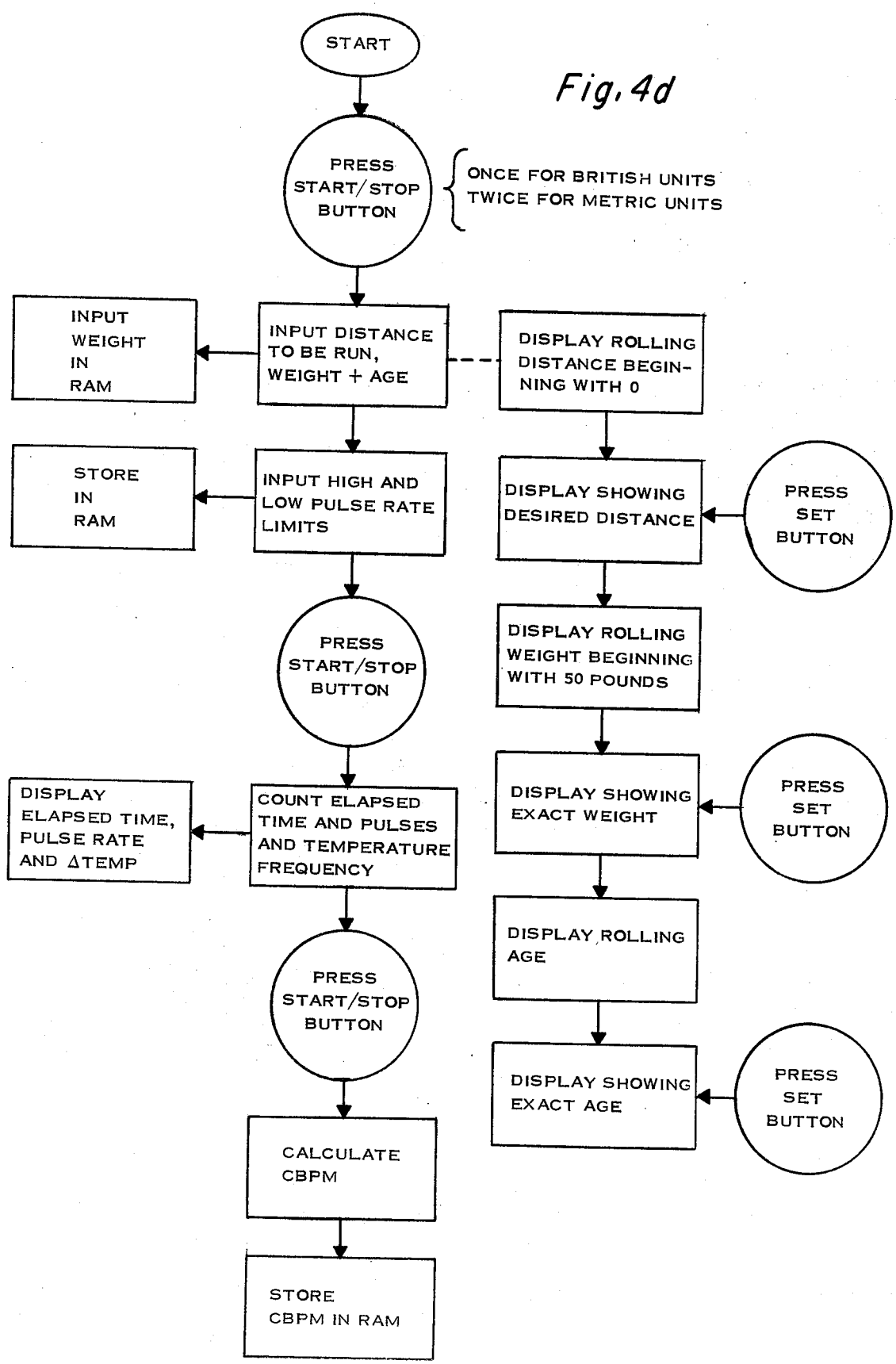
Figure 4E:
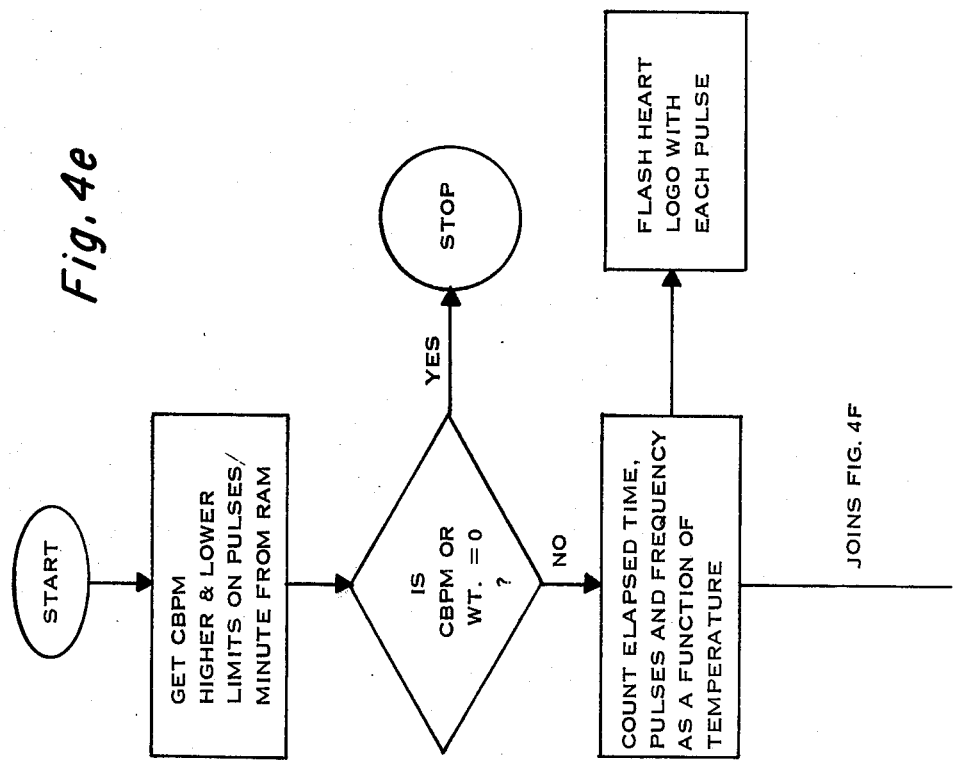
Figure 4H:
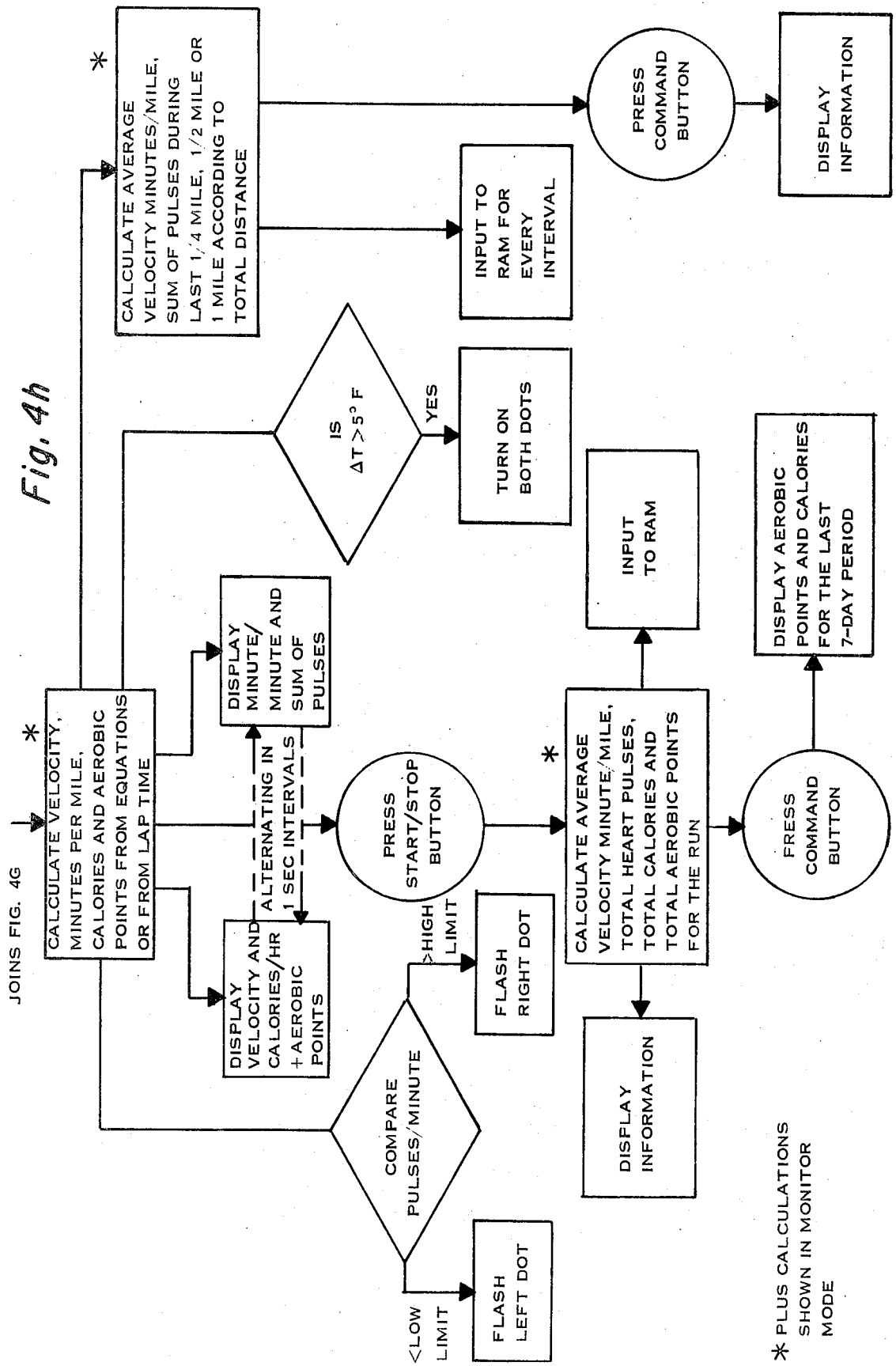
Figure 4I:
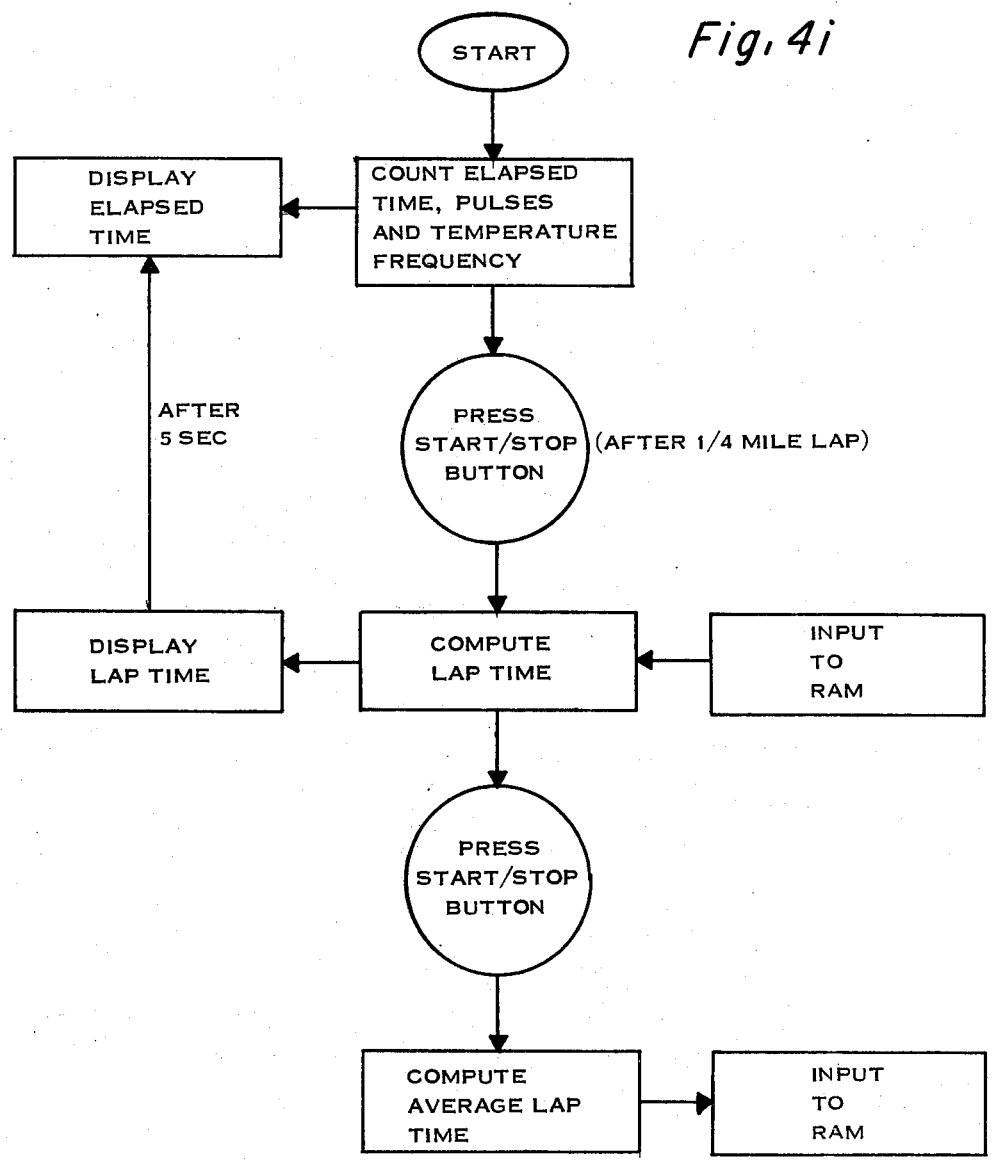

To shift instrument 11 from mode 1 to a calibration mode (mode 4), mode select switch 18 is pressed three times as shown in FIG. 4b. The user is able to program instrument 11 to calculate and display various parameters in either the English system or the metric system as illustrated in FIG. 4d. If the user desires to use the English system, he presses start/stop switch 19 once and enters distance in miles and weight in pounds. If he wants instrument 11 to display metric units, he presses start/stop switch 19 twice and enters distance in kilometers and weight in kilograms.

To calibrate instrument 11, the user must perform a calibration run over a known distance. When calibrate/set switch 20 is pressed initially (once or twice depending on the measurement system selected), upper display 15a displays sequentially increasing distances beginning at zero. When the calibration distance is displayed, the user presses calibrate/set switch 20 again, thereby causing lower display 15b to begin cycling through body weights beginning at 50 pounds (or the equivalent in kilograms). When the user's correct weight is displayed, calibrate/set switch 20 is pressed again whereupon the user enters his age. Once the correct age is entered, calibrate/set switch 20 is pressed again and the user enters the high and low pulse rate limits. Start/stop switch 19 is pressed to activate an elapsed time counter within digital processor 27 at the start of the calibration run.

During the run, instrument 11 displays only elapsed time, pulse rate and change in temperature ($\Delta T$). Digital processor 27 counts the total number of heart beats during the calibration exercise and determines the total heart beats per mile, i.e. calibration heart beats per mile (CBPM), according to the following formula:

$$CBPM = \frac{SHB - AF(t) - Tc - .7(t)}{Distance} \qquad (8)$$

where

SHB = sum of the heart beats during the calibration exercise

AF(t) = age compensation factor expressed as a reference pulse rate

Figure 5A:
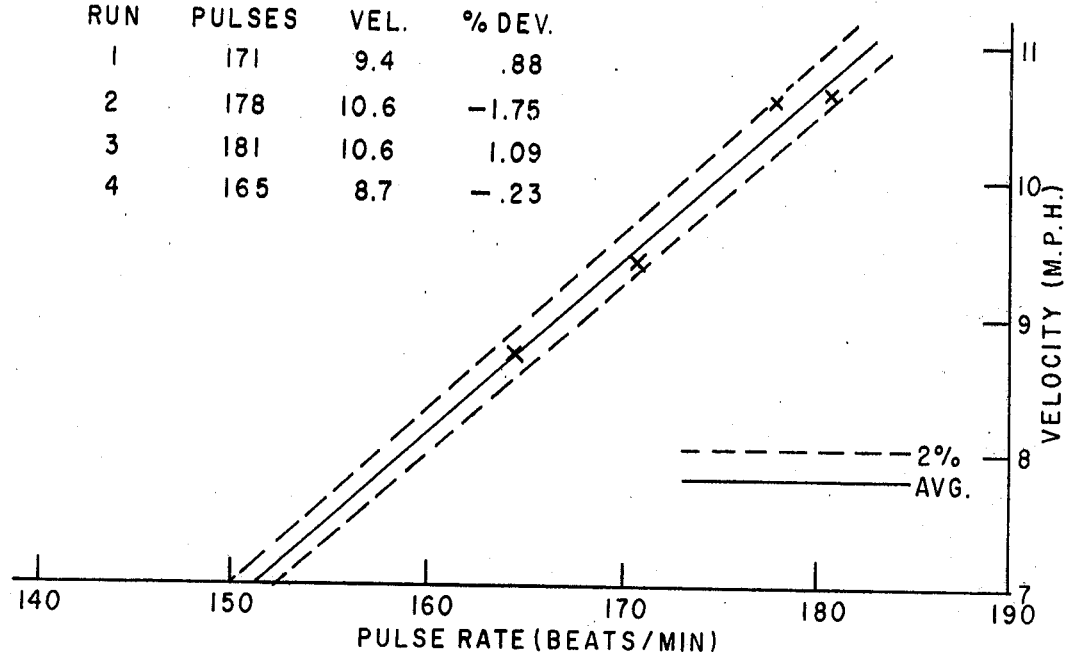
FIGS. 5*a* and 5*b* are graphs showing pulse rate vs. velocity profiles for a 26 year old athlete and a 49 year old athlete, respectively, engaged in physical exercise.
Figure 5B:
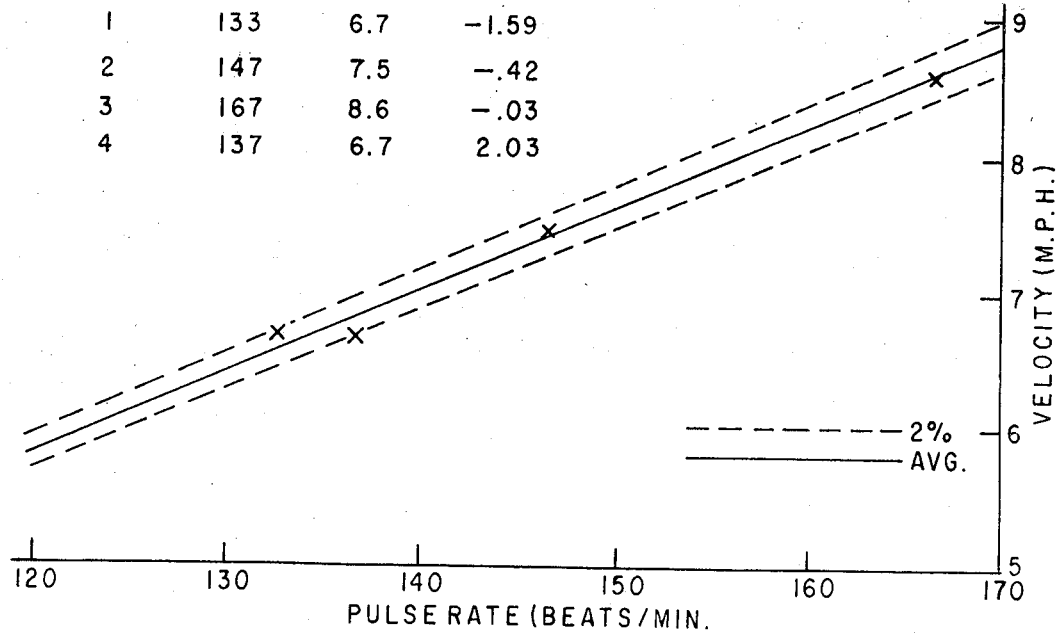

TC = temperature compensation factor 0.7(t) = compensation factor derived to account for the transition of the body from aerobic to anaerobic oxygen supply determined by multiplying 0.7 heart beats/minute times the elapsed exercise time in minutes. AF represents a reference pulse rate which is related to the user's age. In general an older person's pulse rate increases more than a younger person's pulse rate as a result of an increase in the body's work rate. For a runner or jogger an increase in velocity represents an increase in the body's work rate and a corresponding increase in pulse rate as shown in FIGS. 5a and 5b. FIG. 5a shows a velocity vs. pulse rate graph for 26 year old runner; FIG. 5b shows a velocity vs. pulse rate graph for a 49 year old runner. The 26 year old runner exhibits less of an increase in pulse rate for an incremental increase in velocity than does the 49 year old runner as indicated by the steeper slope in FIG. 5a. Moreover, physiological statistics have shown that the slope of the velocity vs. pulse rate profile is predictable based on the runner's age. Using empirical data on velocity vs. pulse rate for athletes of various ages, an empirical relationship between reference pulse rate (intercept pulse rate at zero velocity point on a velocity vs. pulse rate graph) and age may be established as exemplified by FIG. 6. The user's age compensation factor, AF, is determined by digital processor 27 in accordance with the empirically-derived relationship between age and reference pulse rate for which it is programmed. The difference between the total number of pulses measured during the exercise period and the age compensation factor AF multiplied by elapsed time is indicative of the increase in the number of heart beats attributable to the user's traversing a given distance. The temperature compensation factor, TC, which accounts for the increase in pulse rate attributable to increased core temperature, is expressed in heart beat units as follows:

$$Tc = \Delta T \cdot 10 \cdot t \qquad (9)$$

where $\Delta T$ = increase in core temperature in °F.

10 = number of heart beats per minute attributable to each 1° F. increase in core temperature.

t = exercise time period (minutes)

When $\Delta T$ is expressed in °C., $Tc = \Delta T \cdot 18 \cdot t$. Using expression (8) digital processor 27 calculates calibration heart beats per mile, which is a function of the amount of work performed by the heart over a one mile distance. Physiological studies have shown that during repeated maximal exercise, an individual's pulse rate is remarkably similar under various conditions, with a standard duration of $\pm 3$ beats per minute. Similarly, an athlete's pulse rate climbs rapidly to a particular level at the beginning of an exercise period and stays relatively stable with a slight upward drift on the order of 0.7 beats/minute thereafter. The particular pulse rate level maintained is primarily a function of the athlete's velocity, an increase in pulse rate being essentially linearly dependent upon an increase in velocity. Thus if the calibration exercise is performed at the user's optimum exercise pace or velocity, the results will be predictive of his pulse rate during subsequent exercises at a similar pace. However, if the user exercises at a substantially slower or faster pace on subsequent occasions, his body is performing at a corresponding lower or higher work rate and his pulse rate will be significantly different from the pulse rate during the calibration run.

Similarly, the total number of heart beats and the given distance travelled by an athlete are functions of the total amount of work done by the body. During the calibration run, an empirical relationship indicative of the increased number of heart beats attributable to the athlete's traversing the calibration distance is established using expression (8). This relationship is the calibration beats per mile, which is used as a reference value for determining the distance travelled by the athlete during a subsequent exercise based on the increased number of heart beats attributable to the athlete's traversing the distance.

As previously mentioned, instrument 11 is programmable for high and low pulse rate limits. Physiological studies have shown that one derives maximum benefit from physical exercise without dangerous overexertion when he maintains his pulse rate within a particular range. For example, a normally healthy 25 year old male may require a sustained pulse rate level of approximately 165 to 185 beats/minute (175 being an average value) during physical exercise to derive maximum benefit therefrom. When instrument 11 is in the calibration mode (mode 4), the high and low pulse rate limits (185 and 165, respectively, for the above example) are set in by the user and stored in digital processor 27. Alternatively, digital processor 27 is programmable for automatically determining the high and low pulse rate limits based on the user's age. During subsequent exercise periods, digital processor 27 compares the user's pulse rate at any given time with the high and low pulse rates and selectively activates high heart beat monitor 16a when the user's pulse rate exceeds the high pulse rate by a predetermined amount and low heart beat monitor 16b when the user's pulse rate is less than the low pulse rate by a predetermined amount. Digital processor 27 activates both high and low heart beat monitors 16a and 16b, respectively, when $\Delta T$ exceeds 5° F. or the equivalent thereof in °C. Thus high and low heart beat monitors 16a and 16b, respectively, serve not only as aids to enable the user to maintain an optimum exercise pulse rate, but also to warn him of the occurrence of an excessive pulse rate and/or temperature condition. In another embodiment ear sensor 13 contains an audible alarm for warning the user if his pulse rate or body temperature is outside the preset limits. In still another embodiment, wrist-mounted unit 12 is eliminated and ear sensor 13 is a self-contained temperature measuring device for monitoring body temperature and audibly warning the user if an excessive temperature condition occurs.

Once instrument 11 is properly set and calibrated, it is ready for normal operation in modes 2 and/or 3. When the user presses mode select switch 18, instrument 11 shifts from the Calibration mode (mode 4) to the Time and Date mode (mode 1). By pressing mode select switch 18 a second and a third time, instrument 11 shifts to the Monitoring mode (mode 2) and the Performance mode (mode 3), respectively. The user selects either mode 2 or mode 3 depending on what information he desires to have displayed. At the start of the exercise period, start/stop switch 19 is pressed, thereby activating digital processor 27 to begin counting pulses and monitoring core temperature. During the exercise period, the user may press mode select switch 18 to alternate between modes 2 and 3. Digital processor 27 computes total number of pulses and the pulse rate on a real time basis and displays these parameters on lower display 15b in modes 3 and 2, respectively, as shown in FIGS. 4a, 4e, 4f, 4g, and 4h. Pulse rate (pulses per minute) is determined by the following expression.

$$\text{Pulse rate } (PR) = \frac{4.60}{y} = \frac{240}{y} \tag{10}$$

where y = the time (seconds) measured for 4 heart beat cycles.

Alternating at one second intervals with the real-time pulse rate on lower display 15b in mode 2 is a real-time indication of $\Delta T$ in either °F. or °C., which is determined by digital processor 27 as previously described with respect to FIGS. 3a and 3b. Similarly, alternating at one second intervals with the total number of pulses on lower display 15b in mode 3 are indications of the number of calories expended and aerobics points earned.

Digital processor 27 determines number of calories expended per hour by solving the following equation.

$$\text{Calories/hour} = 1.2\{0.53[W_t(2.3 + 0.32(V - 25)1.65)]\} + 423 \tag{11}$$

where
$W_t$ = the user's body weight in kilograms
$V$ = the user's velocity in kilometers per hour To enter the user's body weight in pounds instead of kilograms in equation (11), Wt (pounds) is divided by 2.205. To enter the velocity in miles/hour instead of kilometers/hour, V (miles/hour) is multiplied by 1.609. Digital processor 27 computes velocity every 15 seconds and solves equation (11) for the number of calories expended during each 15 second interval. The result obtained is divided by 240, i.e. 4 computations per minute, multiplied by 60 minutes. Digital processor 27 cumulates the number of claories expended during each 15 second interval to arrive at the total number expended during the exercise period.

The system of aerobics points was developed by Dr. Kenneth Cooper in a series of popular exercise books (*Aerobics* (1968); *The New Aerobics* (1970); *Aerobics For Women* (1972); and *The Aerobics Way* (1977) as a means of quantifying the amount of and the benefit derived from physical exercise.

Aerobics points are calculated as follows:

$$\text{Aerobics Points } (AP) = \frac{V_A \times D}{1.4} \tag{12}$$

where
$V_A$ = the average velocity during a given time period
$D$ = distance travelled during the given time period.

Digital processor 27 is programmable for calculating aerobics points earned during selected time intervals, such as, for example, 5 minute intervals, and cumulating the total number of points earned during successive intervals.

When instrument 11 is being operated in mode 2, real-time indications of elapsed time and total distance travelled are displayed alternately at one second intervals on upper display 15a. When elapsed time is less than one hour, it is displayed in minutes, seconds and hundredths of seconds. When elapsed time exceeds one hour, it is displayed in hours, minutes and seconds. Digital processor 27 measures the total number of heart beats and the elapsed time and calculates distance traveled according to the following expression.

$$\text{Distance (miles)} = \frac{SHB - AF(t) - Tc - .7(t)}{CBPM} \quad (13)$$

where
SHB = total pulses during the exercise period
AF(t) = age compensation factor
TC = temperature compensation factor (see expression (9))
0.7(t) = compensation factor for transition from aerobic to anaerobic oxygen supply (see expression (8))
CBPM = calibration beats per mile from calibration exercise.

As previously mentioned, the total distance travelled by an athlete such as a runner or jogger is a function of the work performed by the heart and hence the increased number of heart beats attributable to the athlete's traversing the distance. Distances are displayed to the nearest hundredth of a mile up to 9.99 miles and alternatively to the nearest hundredth of a kilometer up to 19.99 kilometers.

When instrument 11 is operated in mode 3, real-time indications of average velocity and minutes per mile, or alternatively, minutes per kilometer, are alternately displayed at one second intervals on upper display 15a. Average velocity (Va) is calculated as follows.

$$Va = \frac{D}{ET} \quad (14)$$
(miles/hr or km/hr)

where
D = distance traveled from expression (13) in miles or kilometers
ET = elapsed time in hours
Minutes per mile (MPM) is calculated as follows.

$$MPM = 60/Va \quad (15)$$

where Va = average velocity in miles/hour. Alternatively, minutes per kilometer (MPK) is calculated as follows:

$$MPK = 60/Va \quad (16)$$

where Va = average velocity in kilometers/hour. In addition to the above-described four modes of operation, instrument 11 also operates in a special Lap mode (FIG. 4g), designed for runners exercising on a standard ¼ mile track. Instrument 11 automatically switches to the Lap mode from either mode 2 or mode 3 when start/stop switch 19 is pressed within 4 minutes after instrument 11 has been started. In this mode, the runner presses start/stop switch 19 as he completes each ¼ mile lap. Instrument 11 computes and displays the individual lap time for 5 seconds after the completion of each lap and counts the total number of laps to determine distance. Instrument 11 will also display information in accordance with the previous mode, i.e. mode 2 or mode 3. To signal the end of the run, the runner presses start/stop switch 19 two times rapidly in succession. Digital processor 27 computes velocity, total distance, aerobics points, calories expended and minutes per mile based on ¼ mile lap increments rather than on the pulse and temperature information as previously described. If the user has calibrated instrument 11 for metric units, a lap distance of 400 yards will be assumed. Table I summarizes information that is displayed during an exercise period in each of the four normal modes of operation plus the Lap mode.

In addition to computing and displaying parameters such as velocity, distance traveled, pulse rate and $\Delta T$ on a real-time basis while the user is exercising, digital processor 27 computes and stores for display after the exercise has been completed the following parameters for each ¼ mile or 0.4 km increment of distance when instrument 11 is in either mode 2 or mode 3.

Velocity in MPH or KPH
Minutes per mile or kilometer
Total heart beats
Pulse rate
$\Delta T$ Digital processor 27 computes and stores for display the following parameters for the entire exercise period:
Average Velocity
Total Distance Traveled
Average minutes per mile or km
Total heart beats
Average pulse rate
Maximum $\Delta T$
Total aerobics points
Total calories expended.

Digital processor 27 will accumulate and store for display for a seven day time period the cummulative totals of aerobics points earned and calories expended.

Table II shows the various parameters (and examples thereof) which are stored in memory of digital processor 27 for display after an exercise has been completed. Data is displayed for each ¼ mile or 0.4 km increment up to a distance of 5 miles. Between 5 and 10 miles, data is displayed for each ½ mile increment. After 10 miles, data is displayed for one mile increments.

The above-described measuring instrument 11 provides real-time indications of important physiological parameters such as pulse rate and body temperature, thereby apprising the user of the relative work load on his heart and the overall physical stress on his body. Using this information, the athlete is able to regulate his exercise pace so as not to overexert to a dangerous degree. In addition instrument 11 provides other information of interest to athletes such as runners and joggers. Distance travelled, velocity, minutes per mile, aerobics points earned and calories expended are calculated based on temperature and pulse data, displayed on a real-time basis during an exercise period and stored for display after the exercise has been completed.

Various embodiments of the invention have now been described in detail. Since it is obvious that many additional changes and modifications can be made in the above-described details without departing from the nature and spirit of the invention, it is understood that the invention is not to be limited to these details except as set forth in the appended claims.

TABLE I

Information Displayed Real-time During an Exercise Period

| Mode | Upper Display 15a | Middle Display 16a and 16b | Lower Display 15b |
|---|---|---|---|
| 1 (Time and Date) | time of day | | calendar date heart beat rate |
| 2 (Monitor) | distance elapsed time | high and low heart beat rate | heart beat rate change in temperature |
| 3 (Performance) | velocity minutes per mile | high and low heart beat rate | calories and aerobics points total heart beats |
| 4 (Calibrate) | calibration distance elapsed time | | heart beat rate change in temperature |
| Lap | lap time (5 second display) Mode 2 or Mode 3 information | | Mode 2 or Mode 3 information |

TABLE II

After an exercise has been completed by stopping the Instrument processor with the Start-Stop button, the memory will provide information for display of the following parameters when the instrument is in the Monitor or the Performance Mode. The information will be displayed in sequence, each information unit remaining on display for five seconds at a time.

| DISTANCE (MARK) ACTUAL (LAP MODE) | MEASURED (NORMAL MODE) | ELAPSED TIME | LAP TIME | PULSES PER MIN | DELTA TEMP. | VELO-CITY | MINUTES PER MILE | PULSES | CALO-RIES | AEROBICS POINTS |
|---|---|---|---|---|---|---|---|---|---|---|
| .25M | .25M | 2 10 13 | 2 10 13 | 156 | 00 | 702 | 8 28 | 300 | 460 | 30 |
| .50M | .50M | 4 15 14 | 2 05 01 | 160 | 01 | 697 | 8 32 | 610 | 485 | 31 |
| — | — | — | — | — | — | — | — | — | — | — |
| 5.00M | 5.00M | 42 16 13 | 2 30 10 | 165 | 04 | 678 | 8 45 | 6015 | 590 | 42 |
| 5.50M | 5.50M | 46 25 14 | 2 25 20 | 167 | 05 | 679 | 8 46 | 6620 | 610 | 47 |
| — | — | — | — | — | — | — | — | — | — | — |
| 10.00M | 10.00M | 1 28 40 | 2 40 | 170 | 1.0 | 667 | 8 50 | 12250 | 701 | 62 |
| 11.00M | 11.00M | 1 37 20 | 2 50 | 171 | 1.2 | 670 | 8 51 | 13410 | 740 | 68 |
| — | — | — | — | — | — | — | — | — | — | — |
| 30.00M Total 30.00M | 30.00M Total 30.00M | 3 45 14 Total 3 45 14 | 2 55 Avg. 2 41 | 178 Aug. 168 | 1.4 Max. 0.8 | 690 Avg. 687 | 8 38 Avg. 8 41 | 37350 Total 37360 | 930 Total 930 | 83 Total 83 |

What is claimed is:

1. A body-mounted measuring instrument for computing velocity and distance travelled by a user engaged in physical exercise as a function of the user's heartbeat and the exercise time, said instrument comprising:

(a) heart beat sensing means for detecting heartbeats of the user and for generating electrical signals representative thereof;

(b) computing means responsive to said electrical signals for counting the number of detected heart beats and for determining the user's velocity and distance travelled during a period of physical exercise in accordance with a program instruction set stored in said computing means, said program instruction set representing a predetermined relationship between the number of detected heart beats during the exercise time and the user's velocity and distance travelled; and (c) display means for displaying the results of selected computations performed by said computing means, said computations including the user's velocity and distance travelled during the exercise.

2. The instrument according to claim 1 further including temperature sensing means for measuring internal body temperature of the user, said computing means being further responsive to said internal body temperature measurement for computing a difference in internal body temperature from a predetermined reference temperature and for calculating the distance travelled by the user based on the computed difference in internal body temperature.

3. The instrument according to claim 2, wherein said computing means determines the distance travelled based on the increased number of heart beats attributable to the user's traversing the distance, said increased number of heart beats representing the difference between the total number of heart beats and the sum of a reference number of heart beats based on the user's age and a number of heart beats attributable to the difference in internal body temperature.

4. The instrument according to claim 3, wherein said computing means is programmed to calculate a plurality of parameters of interest to an athlete user based on the total number of heartbeats, the distance travelled and elapsed time, said plurality of parameters including the athlete's velocity, minutes per mile, calories expended, and aerobic points earned, said display means for displaying said parameters to the user.

5. The instrument according to claim 4, wherein said computing means is programmed for a plurality of user-selected display modes, said computing means being responsive to the particular mode selected for controlling said display means to display specific parameters of interest to the athlete.

6. The instrument according to claim 1, wherein said computing means is comprised of a digital processor means, said digital processor means having memory means for storing program instructions and data which is being processed by said digital processor means and arithmetic logic means for performing mathematical operations on the data stored in said memory means in accordance with program instructions stored therein.

7. A body-mountable apparatus for determining a plurality of exercise-related parameters based on the time required for a user to traverse a predetermined distance, said apparatus comprising:
(a) memory means having a predetermined distance increment stored therein;
(b) user activatable input means for transmitting an electrical signal indicating that the user has traversed the distance increment;
(c) timekeeping means for keeping track of elapsed time during the exercise period;
(d) processing means responsive to said electrical signal and to elapsed time information for determining a plurality of exercise-related parameters for the user for the exercise period, said parameters including the user's velocity in distance per unit time and the user's exercise pace in time per unit distance; and
(e) output indicator means for providing an indication of said determined parameters to the user.

8. The apparatus according to claim 7 wherein said indicator means is a digital display for displaying said determined paratmeter to the user.

9. The apparatus according to claim 7 wherein said apparatus includes means for mounting said apparatus on one of the user's wrists, said means for mounting having substantially the same size and shape as a wrist watch.

10. The apparatus according to claim 7 wherein said processing means includes means for determining velocity in miles per hour, exercise pace in minutes per mile, total calories expended and aerobic points earned for the distance increment traversed by the user, said output indicator means for providing indications of the determined parameters to the user.

11. The apparatus according to claim 7 wherein said memory means includes means for storing a plurality of distance increments sequentially therein, said input means being activated each time the user traveres a respective distance increment.

12. The apparatus according to claim 11 wherein said processing means includes means for determining said exercise-related parameters for each of said distance increments and for the cumulative total thereof, said output indicator means for providing indications of the determined parameters to the user upon the completion of each individual distance increment and the total thereof.

13. A body-mountable instrument for determining distance travelled by a user engaged in physical exercise as a function of the user's heart beat and exercise time, said instrument comprising:
(a) heart beat sensing means for detecting the user's heart beats and providing electrical signals indicative thereof;
(b) processing means responsive to said electrical signals for counting the total number of detected heart beats and for determining the distance travelled by the user during the exercise period based upon the counted heart beats; and
(c) output indicator means for providing an indication of the determined distance to the user.

14. The instrument according to claim 13 wherein said processing means is comprised of digital processor means, said digital processor means including timekeeping means for keeping track of elapsed time, said digital processor means being responsive to said detected heart beats for computing a plurality of exercise-related parameters, including the user's exercise pace in time per unit distance and the calories expended and aerobics points earned by the user during the exercise period, in accordance with a stored instruction set, said output indicator means for providing indications of said determined parameters to the user.

15. The instrument according to claim 14 wherein said output indicator means is comprised of a digital display for providing a visual display of said determined parameters for the user.

16. The instrument according to claim 13 wherein said instrument includes means for mounting said instrument on the user's wrist and having substantially the same size and shape as a wrist watch.

17. The instrument according to claim 13 wherein said processing means includes means for determining the user's cumulative distance on a real-time basis, said indicator means for providing an indication of the cumulative distance travelled by the user on a real-time basis and at the end of the exercise period.

18. A body-mountable instrument for determining a user's velocity during an exercise period as a function of the rate at which the user's heart is beating during the exercise period, said instrument comprising:
(a) heart beat sensing means for detecting the user's heart beats and providing electrical signals indicative thereof;
(b) timekeeping means for keeping track of elapsed time;
(c) processing means responsive to said electrical signals and to elapsed time information for computing the user's heart rate and for determining the user's velocity based on the computed heart rate; and
(d) output indicator means for providing an indication of the determined velocity to the user.

19. The instrument according to claim 18 wherein said processing means includes means for determining the user's velocity on a real-time basis during the exercise period and the user's average velocity for the entire exercise period upon the completion thereof, said output indicator means for providing indications of said real-time velocity and said average velocity to the user.

20. The instrument according to claim 19 wherein said processing means is comprised of digital processor means, said digital processor means being responsive to said detected heart beats and elapsed time information for computing a plurality of exercise-related parameters, including the user's velocity, distance travelled, exercise pace, calories expended and aerobics points earned during the exercise period, in accordance with a stored instruction set, said indicator means for providing indications of said determined parameters to the user.

21. The instrument according to claim 20 wherein said output indicator means is a digital display for providing a visual display of said determined parameters.

22. The instrument according to claim 21 wherein said instrument includes user controllable switch means for allowing the user to control the mode of operation of the instrument and select the parameters to be displayed.

23. The instrument according to claim 18 wherein said instrument includes means for wrist-mounting said instrument in substantially the same size and shape as a wrist watch.

* * * * *